United States Patent [19]

Demers et al.

[11] Patent Number: 5,066,658

[45] Date of Patent: Nov. 19, 1991

[54] SUBSTITUTED HYDROXYUREAS

[75] Inventors: James P. Demers, New York, N.Y.; Richard B. Sulsky, Somerville, N.J.

[73] Assignee: Ortho Pharmaceutical Corporation, Raritan, N.J.

[21] Appl. No.: 477,000

[22] Filed: Feb. 7, 1990

Related U.S. Application Data

[63] Continuation-in-part of Ser. No. 269,808, Nov. 10, 1988, abandoned, which is a continuation-in-part of Ser. No. 21,815, Mar. 4, 1987, abandoned.

[51] Int. Cl.$^5$ .............. A61K 31/505; A61K 31/415; C07D 239/02; C07D 235/30
[52] U.S. Cl. .................................. 514/269; 514/274; 514/392; 514/863; 544/318; 544/298; 548/307
[58] Field of Search ............... 544/318, 298; 548/307; 514/269, 274, 392, 863

[56] References Cited

U.S. PATENT DOCUMENTS 4,618,692 10/1986 Scheffler et al. .................... 544/57

OTHER PUBLICATIONS

Chou et al., CA87-83966q (1977).
Sulsky et al., Chem. Abst. 112-216835e (1990).

*Primary Examiner*—Cecilia Shen
*Attorney, Agent, or Firm*—Benjamin F. Lambert

[57] ABSTRACT

The present invention relates to substituted hydroxyureas. These compounds inhibit the enzyme 5-lipoxygenase. In addition, certain of the compounds also inhibit the enzyme-cyclooxygenase. The compounds are useful for treating asthma, allergies, arthritis, posoriasis, ischemia, dermatitis, inflammation and/or broncho-constriction and/or inflammatory diseases of the eye.

10 Claims, No Drawings

SUBSTITUTED HYDROXYUREAS

CROSS REFERENCE TO RELATED APPLICATION

This application is a continuation-in-part of U.S. Pat. application Ser. No. 269,808 filed Nov. 10, 1988, now abandoned, which in turn is a continuation-in-part of U.S. Pat. application Ser. No. 21,815, filed Mar. 4, 1987, now abandoned.

BACKGROUND OF THE INVENTION

1. Field of the Invention

The present invention relates to substituted hydroxyureas as described further below. These compounds inhibit the enzyme 5-lipoxygenase. In addition, certain of the compounds also inhibit the enzyme cyclooxygenase. The compounds are useful for treating asthma, allergies, arthritis, psoriasis, ischemia, dermatitis, inflammation, bronchoconstriction and/or inflammatory diseases of the eye.

2. Description of the Prior Art

European Patent Application 196,184 describes an exceedingly vast array of compounds which may include hydroxyureas. The generic disclosure consists of the following structures:

$$R-(CO)_n-N(OR_1)-(CO)_m-R_2$$

and

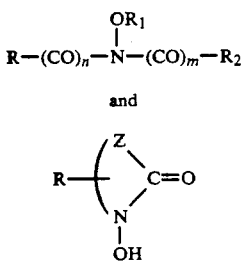

where R may be a variety of aryl-arkyl or aryl-alkenyl groups, n may be 0, m may be 1, $R_1$ may be H and $R_2$ may be amino, arylamino or lower alkylamino. For the cyclic cases, Z is defined as a $C_2-C_5$ alkylene chain in which one of the carbon atoms may be replaced by a hetero atom. The compounds are lipoxygenase and/or cyclooxygenase inhibitors and are said to be useful in treating a large variety of disorders. See column 13, line 21–column 14, line 36 and column 15, line 1–column 18, line 4.

Hydroxyureas substituted by $C_1-C_8$ alkyl groups are well known in the literature as inhibitors of ribonucleotide reductase (Parker et al., *J. Pharm.Sci.* 66. 1040 (1977), Larsen et al., *Eur. J. Biochem.* 125, 75 (1982), and consequently as anti-mitotic agents (Yu et al., *J. Invest. Dermatol.* 63, 279 (1974) and as inhibitors of seed germination (Clifton et al., *Life Sci.* 7, 993 (1968). Due to their anti-oxidant properties, they are also known as stabilizers for photographic developer compositions, e.g., FR 2,184,047, DE 2,638,525 and DE 1,926,658. U.K. 921,536 describes a process for preparing hydroxyureas of the formula RNHCON(R')OH. Hydroxyureas substituted by one or more aryl groups are also well known, due to the ready availability of aryl isocyanates.

Hydroxyureas substituted with $C_8$ and above alkyl groups or aryl-alkyl groups are less known. The cases where $R_1$ and/or $R_2$ are higher alkyl have been disclosed in several patents as a photographic stabilizer, e.g., DE 2,140,462, DE 2,415,603 and U.S. Pat. No. 4,330,606. The cases where $R_1$ and/or $R_2$ are aryl-alkyl were generically disclosed as photo-stabilizers in the patents noted immediately above.

U.S. Pat. Nos. 4,339,515 and 4,330,606 generically disclose aralkyl hydroxyureas of the formula

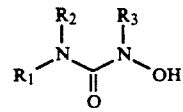

where $R_1$ can be aralkyl. The preferred aralkyl groups contain no more than two carbon atoms in the aliphatic chain (i.e., benzyl and phenylethyl). The U.S. Pat. No. 4,330,606 patent discloses that the aralkyl groups may be substituted with the usual substituents. Methoxy is among the substituents mentioned. Both patents disclose the use of hydroxyureas in photographic emulsions or the process 23 stabilizing such emulsions with hydroxyureas. These two patents refer to U.S. Pat. No. 3,893,863 and U.S. Pat. No. 3,887,376 as prior art regarding hydroxyureas. Both U.S. Pat. No. 3,893,863 and U.S. Pat. No. 3,887,376 disclose compounds of the above formula where $R_1$ is phenyl, p-methylphenyl, p-methoxyphenyl or p-chlorophenyl.

DE 2,845,967 (to VEB Fahlberg-List) discloses in broad terms ureas which may be substituted with, among other groups, hydroxy and aralkyl, as plant virucides.

U.S. Pat. No. 4,618,692 discloses alkyl and aralkyl hydroxyureas, which are used as intermediates in the preparation of 4-carbamoyloxy-1,3,2-oxazaphosphorins. Substantially identical disclosures are in Belgian Patents BE 899,457 and BE 900,370. Specifically disclosed is the structure

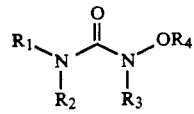

where $R_1$ may be benzyl, 1-phenylethyl or 2-phenylethyl, and $R_2$ and $R_3$ may be hydrogen.

Some related technology is described in several patents disclosing hydroxamic acids, which are lipoxygenase inhibitors useful as anti-allergy and anti-inflammatory agents. These are U.S. Pat. Nos. 4,604,407, 4,607,053, 4,605,669, 4,623,661, 3,853,905, 3,890,377, 3,972,934 and 4,001,322, and European patent application 196,674.

SUMMARY OF THE INVENTION

A hydroxyurea selected from the following formulae:

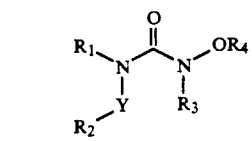

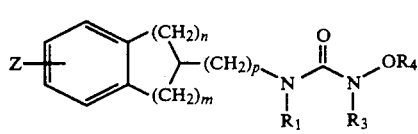

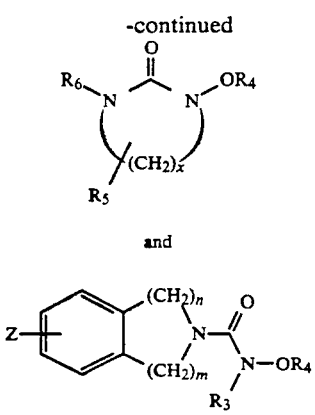

and

III

IV where $R_1$ is H, aryl, or lower alkyl, $R_2$ is lower alkoxycarbonyl, 1,4-benzodioxan-6-yl, 1,3-benzodioxol-5-yl, [1,1'-biphenyl]-4-yloxy, substituted aryl, or substituted aryloxy, wherein the substituent is $C_1$-$C_{20}$ alkyl, $C_2$-$C_{20}$ alkenyl, $C_1$-$C_{20}$ alkoxy, $C_3$-$C_{20}$ alkenyloxy, aryl lower alkoxy, lower cycloalkyl, aryloxy, lower cycloalkyloxy, hydroxy, or halogen.

Y is $(CH_2)_n$ where n is 1 to 7, or a lower cycloalkyl or bicycloalkyl diradical such as a bicyclo[2.2.1]-5-heptene-2,3-diyl or a bicyclo[2.2.1]-5-heptane-2,3-diyl radical.

$R_3$ is $C_1$-$C_{20}$ alkyl, or substituted $C_1$ to $C_{20}$ alkyl wherein the substituent is lower alkoxycarbonyl.

$R_4$ is hydrogen or lower acyl.

$R_5$ is $C_5$ to $C_{10}$ alkyl or lower alkoxycarbonyl.

$R_6$ is $C_1$ to $C_{10}$ alkyl.

Z is $C_1$-$C_{20}$ alkyl, $C_2$-$C_{20}$ alkenyl, $C_1$-$C_{20}$ alkoxy, $C_3$-$C_{20}$ alkenyloxy, lower cycloalkyl, lower cycloalkyloxy, hydroxy, or halogen.

x is 2 or 3.

p is 0 or 1.

m is 1 or 2.

n is 0, 1 or 2.

The compounds of formulas I-IV inhibit 5-lipoxygenase and are useful as bronchodilators. In addition, certain of the compounds also inhibit the enzyme cyclooxygenase. The compounds are useful for treating asthma, allergies, arthritis, psoriasis, ischemia, dermatitis, inflammation, bronchoconstriction and/or inflammatory diseases of the eye.

DETAILED DESCRIPTION OF THE INVENTION

The invention in its broadest aspects relates to substituted hydroxyureas or substituted O-acylated hydroxyureas. The latter compounds can serve as prodrugs by deacylation in vivo. The compounds are inhibitors of 5-lipoxygenase and/or cyclooxygenase and are useful in treating diseases in which these enzymes play a role, apparently by modulating the biosynthesis of leukotrienes. The hydroxyureas demonstrating this inhibitory activity are shown by formulas I-IV above.

The term "alkyl" includes straight- or branched-chain radicals.

The term "alkenyl" includes the alkyl groups as described above which also include one to four carbon-carbon double bonds within the chain.

The terms "aryl-alkyl" and "aryl-alkenyl" include $C_1$-$C_{20}$ alkyl or $C_2$-$C_{20}$ alkenyl groups, respectively, substituted by aryl at any position.

The term "aryl" includes benzene and naphthalene rings.

The preferred compounds are those of Formula III where $R_4$ is H.

The compounds of formula I can be prepared by reacting a carbamoyl chloride of the formula

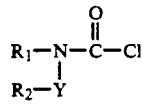

or an isocyanate of the formula $R_2$—Y—N=C=O with a hydroxylamine of the formula $R_3$—NHOR$_7$ where $R_7$ may be H or a protecting group in an inert solvent. When a carbamyl chloride is used, the reaction is carried out in the presence of a base. Suitable inert solvents include tetrahydrofuran, dimethylformamide, methylene chloride, toluene and the like. The preferred base is triethylamine. Suitable protecting groups are acetyl or benzyl. A hypernucleophilic acylation catalyst such as 4-dimethylaminopyridine can also be used. The resultant compounds, when $R_1$ or $R_3$ is H, can be N-alkylated if desired when the hydroxyl group is suitably protected. Following the synthesis of the O-protected hydroxyurea, the protecting group is removed by conventional techniques. The O-acylated derivatives can be prepared in a conventional manner or by using the O-acylated hydroxylamine as the reactant.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral, parenteral, aerosol or topical. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit, e.g., tablet, capsule, powder, injection, teaspoonful and the like, from about 0.01 to about 100 mg/kg, and preferably from about 0.1 to about 50 mg/kg of the active ingredient.

The following examples describe the invention in greater particularity and are intended to be a way of illustrating but not limiting the invention.

EXAMPLE 1

N,N-Diethyl-N'-decyl-hydroxyurea

To a stirred solution of N-decylhydroxylamine (2.60 g, 15.0 mmol) and triethylamine (2.3 ml) in tetrahydrofuran (hereinafter THF) (30 ml) at 0° C. was added dropwise N,N-diethylcarbamyl chloride (1.92 ml). After two hours, 4-(dimethylamino)pyridine (1.3 g) was added. After 18 hours, the reaction mixture was quenched with 1N hydrochloric acid (hereinafter HCl), extracted with hexane, and the organic solution was dried over MgSO4, filtered and evaporated. Trituration of the residue with hexane at −30° C. gave the title compound as a while solid (3.1 g, mp 35°-37° C.).

EXAMPLE 2

N-Methyl-N'-decyl-N'-hydroxyurea

To a stirred solution of di-t-butyldicarbonate (15.98 g, 73.2 mmol) in dioxane (75 ml) was added benzyloxyamine hydrochloride (11.7 g, 1.0 equiv.) and a solution of Na2CO3 (7.8 g) in water (75 ml). After 16 hours, the solution was partially evaporated to remove dioxane, and the residue was acidified with citric acid to pH 3. After extracting twice with ether, the extracts were dried (MgSO4), filtered and evaporated, to give t-butyl N-benzyloxycarbamate as a colorless oil which solidified (16.02 g, 98% yield). To this urethane (6.53 g, 29.2 mmol) in dimethylformamide (hereinafter DMF) (45 ml) under nitrogen at room temperature was added sodium hydride (1.29 g of a 60% dispersion in mineral oil). Gas evolved, and the colorless solution was stirred for 30 minutes. 1-Bromodecane (6.66 ml) was then added, and the mixture was heated to 70° C. After one hour, the mixture was poured into water (150 ml) and extracted twice with ether. The extracts were combined, washed with water and brine, dried (MgSO4), and evaporated.

Purification by chromatography on silica gave t-butyl N-benzyloxy-N-decylcarbamate as a colorless oil (8.39 g, 79% yield). To a solution of this urethane (7.0 g) in methylene chloride (15 ml) at room temperature under nitrogen was added trifluoroacetic acid (15 ml). After 30 minutes, the solution was evaporated at 40° C. 1N NaHCO3 was added and solid Na2CO3 was added to bring the pH to 9. The mixture was extracted twice with methylene chloride, and the combined extracts were dried (MgSO4), filtered, and evaporated to give decyl-N-benzyloxyamine as a colorless oil (5.0g g, 100% yield). To a stirred solution of this amine (4.92 g, 18.8 mmol) in methylene chloride (30 ml) at room temperature under nitrogen was added methyl isocyanate (1.2 ml). After two hours, the reaction mixture was evaporated and triturated with cold pentane to give N-benzyloxy-N-decyl-N'-methylurea as a white solid (4.98 g, 83% yield). This urea (745 mg) was dissolved in ethanol (10 ml) under nitrogen at room temperature, and ammonium formate (0.8 g) was added. After 20 minutes, 10% palladium on carbon (0.25 g) was added. After stirring for two hours, the reaction mixture was filtered through celite and evaporated. Water was added, and the resulting solid was collected by filtration. Recrystallization from isopropanol gave the title compound as a white solid (420 mg, mp 96°-97° C.).

EXAMPLE 3

N-(Ethoxycarbonyl)methyl-N'-decyl-N'-hydroxyurea

Using the method of Example 2 above, but using ethyl-2-isocyanatoacetate, the title compound was obtained and recrystallized from water-ethanol, mp 70°-71° C.

EXAMPLE 4

N-[2-(Methoxycarbonyl)ethyl]-N'-decyl-N'-hydroxyurea

Using the method of Example 2 above, but using methyl 3-isocyanatopropionate, the named compound was obtained and recrystallized from pentane-methylene chloride, mp 77°-78° C.

EXAMPLE 5

N-[3-(Methoxycarbonyl)propyl]-N'-decyl-N'-hydroxyurea

Using the method of Example 2 above, but using methyl 4-isocyanatobutyrate, the title compound was obtained and recrystallized from methylenechloride-hexane, mp 89°-90° C.

EXAMPLE 6

N-[6-(Methoxycarbonyl)hexyl]-N'-decyl-N'-hydroxyurea

Using the method of Example 2 above, but using methyl 7-isocyanatoheptanoate, the named compound was obtained and recrystallized from hexane-methylene chloride, mp 81°-82° C.

EXAMPLE 7

N,N-Dimethyl-N'-octyl-N'-hydroxyurea

To a stirred slurry of benzyloxyamine hydrochloride (3.19 g, 20 mmol) in the THF (40 ml) at room temperature under nitrogen was added triethylamine (6.13 ml). This slurry was stirred, and dimethylcarbamyl chloride (1.84 ml) was added rapidly. 4-(N,N-dimethylamino)-pyridine (1.0 g, 0.4 equiv.) was added, and the mixture was stirred for 20 hours. The mixture was filtered, and the filtrate evaporated. Purification by chromatography on silica provided N,N-dimethyl-N'benzyloxyurea as a colorless oil (1.62 g, 42% yield).

To a solution of this urea (1.59 g, 8.19 mmol) in DMF (13 ml) at 50° C. under nitrogen was added sodium hydride (360 mg of a 60% dispersion in oil). The resulting solution was stirred for 45 minutes, and 1-bromooctane (1.83 ml) was added. After 16 hours, the mixture was poured into 1% aqueous citric acid (75 ml) and extracted 3 times with 1:1 hexane-ether. The combined extracts were dried (MgSO4), filtered, and evaporated. Purification by chromatography on silica provided N-benzyloxy-N-octyl-N',N'-dimethylurea as a colorless oil (2.04 g, 81% yield). Hydrogenolysis as in Example 2 above, and recrystallization from hexane at −40° C., provided the title compound as a white solid (875 mg, 57% yield), mp 29°-30° C.

EXAMPLE 8

N,N-Dimethyl-N'-nonyl-N'-hydroxyurea

Using the method of Example 7 above, but using 1-iodononane, the title compound was obtained and recrystallized from hexane, mp 30°-40° C.

EXAMPLE 9

N,N-Dimethyl-N'-heptyl-N'-hydroxyurea

Using the method of Example 7 above, but using 1-bromoheptane, the named compound was obtained as a white solid, mp 30°-31° C.

EXAMPLE 10

N,N-Dimethyl-N'-hexyl-N'-hydroxyurea

Using the method of Example 7 above, but using 1-iodohexane, the title compound was obtained as a colorless liquid, mp 19°-20° C.

EXAMPLE 11

N,N-Dimethyl-N'-decyl-N'-hydroxyurea

To a stirred slurry of N-decylhydroxylamine (1.71 g, 9.91 mmol) in the THF (20 ml) at room temperature under nitrogen was added triethylamine (1.51 ml, 1.1 equiv.). The reaction mixture was cooled to 5° C. and dimethyl carbamyl chloride (0.92 ml, 1.05 equiv.) was added dropwise over five minutes. After stirring for two hours, the mixture was poured into 1% aqueous citric acid, and worked up as in Example 1 above. Trituration with pentane gave the named compound as a white solid (2.15 g, 89% Yield), mp 44°-45° C.

EXAMPLE 12

N,N-Dimethyl-N'-undecyl-N'-hydroxyurea

Using the method of Example 7 above, but using 1-iodoundecane, provided the title compound, recrystallized from ethanol-water, mp 54°-55° C.

EXAMPLE 13

N,N-Dimethyl-N.-dodecyl-N'-hydroxyurea

Using the method of Example 7 above, but using 1-bromododecane, the named compound was obtained and recrystallized from hexanes, mp 51°-52° C.

EXAMPLE 14

N,N-Dimethyl-N'-tridecyl-N'-hydroxyurea

Using the method of Example 7 above, but using 1-bromotridecane, gave the title compound, recrystallized from hexanes, mp 57°-58° C.

EXAMPLE 15

N,N-Dimethyl-N'-tetradecyl-N'-hydroxyurea

Using the method of Example 7 above, but using 1-bromotetradecane, the named compound was obtained and recrystallized from hexanes, mp 64°-66° C.

EXAMPLE 16

N-Decyl-N'-methyl-N'-hydroxyurea

To a solution of decyl isocyanate (19.6 g, 0.11 mol) in 1,2-dichloroethane (100 ml) was added a solution of benzyloxyamine (0.114 mol) in methylene chloride (100 ml). The solution was refluxed for 20 minutes, evaporated, and the residue triturated with pentane to give N-benzyloxy-N'-decylurea as a white solid (22.36 g, 67% yield). This urea (2.95 g, 10 mmol) was dissolved in DMF (30 ml) at 40° C. Sodium hydride (425 mg of a 60% dispersion in oil) was added. Within 15 minutes, a precipitate formed. After 30 minutes, methyl iodide (0.64 ml) was added, and the mixture was stirred for one hour at room temperature. The resulting solution was poured in 1% HCl, and the resulting solid was washed with water, collected by filtration, and air-dried. Recrystallization from pentane provided N-benzyloxy-N-methyl-N'-decylurea as a white solid (2.25 g, 73% yield). Hydrogenolysis as in Example 2 above, and recrystallization from ethanol-water, provided the title compound as a white solid (1.43 g, 91% yield), mp 74°-76° C.

EXAMPLE 17

N-Decyl-N,N'-dimethyl-N'-hydroxyurea

N-Benzyloxy-N'-decylurea from Example 16 above (2.95 g, 10 mmol) was dissolved in DMF (30 ml), and sodium hydride (420 mg of a 60% dispersion in oil) was added. After 30 minutes, methyl iodide (0.65 ml) was added. The reaction was stirred for one hour, and a second portion of sodium hydride dispersion (420 mg) was added. The reaction was stirred for 30 minutes, and a second portion of methyl iodide (0.65 ml) was added. After 30 minutes, the mixture was heated to 50° C., and after three hours a clear solution formed. To this solution was added sodium hydride (72 mg of a 60% dispersion), and the mixture stirred for 30 minutes. Methyl iodide (0.5 ml) was added, and the mixture stirred for 24 hours. The mixture was cooled, poured into water, and extracted twice with ether. The extracts were combined, washed with 10% NaHSO$_3$, dried (MgSO$_4$) and filtered. Evaporation gave a colorless oil. Pentane was added, and the solution was cooled to −78° C., then warmed to 0° C. A solid formed, which was removed by filtration. The filtrate was evaporated, to give nearly pure N,N'-dimethyl-N-decyl-N'benzyloxyurea (2.02 g) as a colorless oil. Hydrogenolysis of this material as in Example 2 above, and recrystallization from pentane, provided the named compound as a white solid (850 mg), mp 49°-50° C.

EXAMPLE 18

N-(9-Decenyl)-N'-methyl-N'-hydroxyurea

To a stirred solution of sodium azide (1.32 g) in water (5 ml) at 0° C. was added a solution of 10-undecenoyl chloride (4.30 ml) in dioxane (10 ml). The mixture was stirred for 45 minutes, and poured into ice water (100 ml). The mixture was extracted twice with benzene (50 ml), and the combined extracts were washed with ice water (25 ml), dried (MgSO$_4$), and filtered. The filtrate was heated to reflux under a Dean-Stark trap, removing the first 30 ml of distillate. After 30 minutes at reflux, the reaction was cooled and evaporated, to provide 9-decenyl icocyanate as a colorless oil. This isocyanate was dissolved in DMF (5 ml) and added to a slurry of N-methylhydroxylamine hydrochloride (1.70 g) and triethylamine (2.84 ml) in DMF (20 ml). After two hours, the reaction mixture was filtered through Celite and quenched with water. The resulting solids were collected by filtration, washed with water, and recrystallized from ethyl acetate to provide the title compound as a white solid (1.35 g), mp 58°-59° C.

EXAMPLE 19

N-Decyl-N'-[3-(ethoxycarbonyl)propyl]-N'-hydroxyurea

Using the method of Example 2 above, but using ethyl 4-bromobutyrate, t-butyl N-[3-(ethoxycarbonyl)-propyl]-N-benzyloxy carbamate was obtained as a colorless oil. This carbamate (6.17 g, 18.8 mmol) was dissolved in 3.3M HCl in ethyl acetate (50 ml) at room temperature under nitrogen. After one hour, the turbid solution was evaporated, and the residue was triturated with hexane. Filtration gave ethyl 4-(benzyloxyamino)-butyrate hydrochloride as a white solid (4.59 g, 93% yield). To a solution of decyl isocyanate (0.92 g) in toluene (50 ml) was added this hydrochloride (1.40 g) in DMF (5 ml). Triethylamine (0.75 ml) was added, and the solution was stirred for one hour. The mixture was washed with 10% aqueous citric acid, and the organic solution was dried ($MgSO_4$), filtered and evaporated. Purification by chromatography on silica gave N'-decyl-N-benzyloxy-N-[3-(ethoxycarbonylpropyl]urea as a colorless oil (1.58 g, 58% yield).

Hydrogenolysis as in Example 2 above provided the title compound, recrystallized from ethanol-water, as a white solid (500 mg), mp 68°-69° C.

EXAMPLE 20

N-(1,1-Dimethyldecyl)-N'-methyl-N'-hydroxyurea

To a solution of 2,2-dimethyldecanoic acid (2.62 g, 12.2 mmol) in methylene chloride (25 ml) was added oxalyl chloride (1.17 ml) and DMF (0.1 ml) at room temperature under nitrogen. After one hour, the reaction was evaporated, and the residue dissolved in acetone (5 ml). This solution was added to a solution of sodium azide (1.2 g) in water (5 ml) at 0° C. After 45 minutes, the mixture was poured into ice water (100 ml), and extracted three times with benzene (50 ml). The extracts were combined, dried ($Na_2SO_4$), and filtered through $MgSO_4$. The filtrate was heated to reflux under a Dean-Stark trap, removing the first 20 ml of distillate. After one hour, the solution was cooled and evaporated, and added to a solution of N-methylhydroxylamine hydrochloride (1.02 g) and triethylamine (1.81 ml) in methylene chloride (25 ml). The mixture was stirred for two hours, evaporated, and redissolved in ethyl acetate. This slurry was filtered, and the filtrate washed with 10% aqueous citric acid, dried ($MgSO_4$), filtered and evaporated. Purification by chromatography on silica provided the title compound as a colorless oil (2.14 g, 68% yield).

EXAMPLE 21

N-(2-Hydroxy-11-dodecenyl)-N'-methyl-N'-hydroxyurea

To a slurry of activated zinc (11.8 g) in refluxing dry benzene (135 ml) was added dropwise a mixture of ethyl bromoacetate (19.96 ml, 0.18 mol) and 10-undecenal (10.09 g, 0.06 mol) in benzene (60 ml). The addition took 90 minutes, and the mixture was refluxed another 90 minutes, cooled to room temperature, and stirred for 16 hours. 12N $H_2SO_4$ (90 ml) was added, and the mixture stirred rapidly for one hour. The mixture was diluted with water (200 ml), and extracted three times with benzene. The combined organic extracts were washed with water, 10% $NaH_2PO_4$, dried ($MgSO_4$), filtered and evaporated.

Purification by distillation (Kugelrohr, 135° C./0.2 torr) gave ethyl 3-hydroxy-12-tridecenoate as a colorless oil (12.3 g, 80% yield). To this ester (10.8 g, 42.2 mmol) in dioxane (50 ml) at room temperature was added 1M NaOH (50 ml). After one hour, the resulting slurry was diluted with water and washed twice with hexane. The aqueous layer was acidified with 10% citric acid, and the resulting solid collected by filtration and dried in vacuo to give 3-hydroxy-12-tridecenoic acid as a white solid, mp 62°-64° C. (8.65 g, 90% yield). To a solution of this hydroxy-acid (8.60 g, 37.6 mmol) in DMF (27 ml) at room temperature were added t-butyldimethylsilyl chloride (10.8 g) and imidazole (9.7 g). The reaction was stirred for 24 hours, poured into ice water (250 ml), and extracted three times with hexane. The extracts were combined, dried (Na ), filtered, and evaporated to give the bis-silyl derivative as a light yellow oil (14.5 g, 84% yield).

To this silyl derivative (1.69 g, 3.7 mmol) in methylene chloride (7 ml) at 0° C. under nitrogen was added oxalyl chloride (0.41 ml) and DMF (0.05 ml). After 30 minutes, the mixture was warmed to room temperature and stirred for 90 minutes. The mixture was concentrated twice from methylene chloride, and the residue dissolved in dioxane (4 ml). This solution was added over two minutes to a solution of sodium azide (400 mg) in water (4 ml) at 0° C. After 45 minutes, the mixture was poured into ice water (70 ml) and extracted three times with benzene (30 ml). The combined extracts were dried over $NaSO_4$ and filtered through $MgSO_4$. The filtrate was refluxed under a Dean-Stark trap, removing the first 20 ml of distillate. After 30 minutes at reflux, the mixture was cooled, evaporated, and dissolved in DMF (5 ml). The DMF solution was added to a solution of N-methylhydroxylamine hydrochloride (333 mg) and triethylamine (0.61 ml) in DMF 10 ml). After stirring for 16 hours, the mixture was poured into water and extracted twice with ether. The extracts were dried ($MgSO_4$), filtered and evaporated. Purification by chromatography ? n silica provided N'-hydroxy-N-[2-(t-butyldimethylsilyloxy)-11-dodecenyl]-N'-methylurea as a as a light Yellow oil (815 mg, 57% yield). To a solution of this silyl ether (810 mg) in THF (5 ml) was added acetic acid (5 ml) and water (1.7 ml). The mixture was stirred for 24 hours, diluted with water (50 ml), and the resulting solid collected by filtration. Recrystallization from ethyl acetate gave the named compound as a white solid (338 mg), mp 105°-106° C.

EXAMPLE 22

N-(4,7,10,13-Nonadecatetraenyl)-N'-methyl-N'-hydroxyurea

To a stirred solution of 90% arachidonic acid (1.79 g, 5.9 mmol) in acetone (5 ml) was added triethylamine (0.85 ml, 1.04 equiv.). The mixture was cooled to −20° C., and ethyl chloroformate (0.57 ml, 1.02 equiv.) was added dropwise so as to keep the temperature below −15° C. The resulting slurry was stirred for 15 minutes, and a chilled solution of sodium azide (0.59 g, 1.05 equiv.) in water (2 ml) was added. After 15 minutes, the mixture was poured into ice water (50 ml), extracted twice with benzene (30 ml), and the combined extracts dried ($Na_2SO_4$), filtered through $MgSO_4$, and the filtrate heated to reflux under a Dean-Stark trap, discarding the first 10 ml of distillate. After 30 minutes at reflux, the solution was cooled and evaporated, and the residue dissolved in DMF (4 ml). This was added to a stirred slurry of N-methylhydroxylamine hydrochloride (500 mg) and triethylamine (0.84 ml) in DMF (6 ml). The mixture was stirred for two hours, poured into water, and extracted twice with ether. The combined extracts were dried ($MgSO_4$), filtered and evaporated. Purification by chromatography on silica provided the title compound as a colorless oil (1.02 g, 50% yield).

EXAMPLE 23

1-pentyl-3-hydroxyimidazolidin-2-one

To a stirred solution of benzyloxyamine (36.63 g, 0.297 mol) in THF (250 ml) was added a solution of 2-chloroethyl isocyanate (25.4 ml, 1.0 equiv.) in THF (50 ml) over 20 minutes. The resulting cloudy solution was refluxed for 10 minutes, cooled and evaporated. Trituration of the residue with ether-hexane gave N-benzyloxy-N'-(2-chloroethyl)urea as a white solid (65.82 g, 97% yield), mp 67°-68° C. after recrystallization from hexane-ether. To a stirred solution of this urea (65.8 g, 0.287 mol) in the THF (500 ml) at room temperature was added sodium hydride (11.8 g of 60% dispersion in oil, 1.02 equiv.) in portions over 30 minutes. The cloudy solution was refluxed for 10 minutes, cooled and evaporated. To the resulting semi-solid was added 2% aqueous citric acid (60 ml) and hexane (250 ml). After vigorous agitation, the resulting solid was collected by filtration and washed with water and hexane, to give 1-benzyloxy-2-imidazolidinone as a tan solid (52.66 g, 93% yield), mp 64°-65° C. after recrystallization from water.

To a stirred solution of this imidazolidinone (4.0 g, 20.8 mmol) in DMF (50 ml) under nitrogen at 50° C. was added sodium hydride (1.0 g of a 60% dispersion in oil). A thick slurry formed at once. After 30 minutes, 1-bromopentane (2.84 ml) was added. After 15 minutes, the resulting clear solution was evaporated, and the residue was partitioned between ether and water. The organic extract was washed with water and brine, then dried (MgSO$_4$), filtered, and evaporated. Purification by chromatography on silica provided 3-benzyloxy-1-pentyl-2-imidazolidinone as a colorless oil (4.15 g, 83% yield). Hydrogenolysis as in Example 2 above provided the title compound, after purification by chromatography on silica, as a white solid, mp 60°-61° C.

EXAMPLE 24

1-Octyl-3-hydroxyimidazolidin-2-one

By the method of Example 23 above, using 1-bromooctane, the title compound was obtained as a white solid, mp 53.5°-55.5° C.

EXAMPLE 25

1-Decyl-3-hydroxyimidazolidin-2-one

By the method of Example 23 above, using 1-bromodecane, the named compound was obtained as a white solid, mp 68°-69° C.

EXAMPLE 26

1-Decyl-3-hydroxy-3,4,5,6-tetrahydro-1H-pyrimidin-2-one

To a solution of 9-decenyl isocyanate, prepared as in Example 18 above from 10.8 ml of 10-undecenoyl chloride in 1,2-dichloroethane (150 ml) at room temperature was added benzyloxyamine (7.2 g). After 20 minutes, the mixture was evaporated, hexane (50 ml) was added, and the mixture cooled to 0° C. The resulting solids were collected by filtration, to provide N-(9-decenyl)-N'-benzyloxyurea as a white solid (7.14 g, mp 53°-55° C.). To a stirred slurry of this urea (3.50 g, 11.65 mmol) in DMF (35 ml) at room temperature under nitrogen was added sodium hydride (490 mg of a 60% dispersion in oil). After one hour, 1,3-dibromopropane (1.45 ml) was added, and the reaction was stirred for two hours. The mixture was poured into 1% aqueous HCl (200 ml), and extracted twice with ether. The combined extracts were washed with water, dried (MgSO$_4$), filtered and evaporated. Purification by chromatography on silica gave 3-decyl-1-benzyloxy-3,4,5,6-tetrahydro-1H-pyrimidin-2-one as a colorless oil (1.92 g, 48% yield). Hydrogenolysis as in Example 2 above provided the title compound as a light magenta solid, after recrystallization from carbon tetrachloride, mp 45°-46° C.

EXAMPLE 27

Ethyl 3-decyl-1-hydroxyimidazolidin-2-one-4-carboxylate

By the method of Example 23 above, but using ethyl 2,3-dibromopropionate, the title compound was obtained after recrystallization from water-ethanol as a white solid, mp 70°-72° C.

EXAMPLE 28

4-Decyl-1-hydroxy-3-methylimidazolidin-2-one

Using the method of Example 23 above, but using methyl isocyanate, N-benzyloxy-N'-methylurea was obtained as a white solid. This was reacted with 1,2-dibromododecane and hydrogenolyzed as in Example 26 above, to provide the title compound, after crystallization from cold pentane, as a white solid, mp 47°-48° C.

EXAMPLE 29

5-Decyl-1-hydroxy-3-methyl-3,4,5,6-tetrahydro-1H-pyrimidin-2-one

To a solution of 2-(hydroxymethyl)-1-dodecanol, prepared by LiAlH4 reduction of dimethyl 2-decylmalonate (2.16 g, 10 mmol) in pyridine (7.5 ml) under nitrogen at 0° C. was added methanesulfonyl chloride (1.55 ml, 20 mmol). The temperature was maintained below 35° C. After three hours, the mixture was quenched with 1% aqueous citric acid and extracted three times with ether. The extracts were combined, dried (MgSO$_4$), filtered and evaporated. Purification by chromatography on silica gave the dimesylate as a white solid (2.15 g). This material was used to alkylate N-benzyloxy-N'-methylurea and hydrogenolyzed as in Example 26 above, to provide the title compound after recrystallization from hexane as an off-white solid, mp 63°-64.5° C.

EXAMPLE 30

N-([1,1'-Biphenyl]-4-ylmethyl)N'hydroxy-N'-methylurea

Oxalyl chloride (1.3 ml, 15 mmol) was added to a suspension of 4-[1,1'biphenyl]ylacetic acid (2.12 g, 10 mmol) in benzene (25 ml), and the mixture was refluxed under nitrogen for 15 minutes. The resulting solution was evaporated and the residue, which solidified, was redissolved in acetone (20 ml). To this solution was added a solution of sodium azide (1.0 g, 15 mmol) in water (10 ml), and the mixture stirred vigorously at room temperature. Benzene (200 ml) was added, and the aqueous layer removed by pipette. The organic solution was then dried (MgsO$_4$), filtered, and after boiling away about 10 ml of the solvent, the mixture was refluxed for one hour. The mixture was concentrated to a yellow Oil, which was dissolved in methylene chloride (50 ml). To this was added a solution prepared by heating N-methylhydroxylamine hydrochloride (0.6 g, 7 mmol) and triethylamine (1.2 ml, 8.6 mmol) in methylene chloride (20 ml). The mixture was stirred for 30 minutes, and the precipitate was collected by filtration and recrystallized from methanol to provide the named compound as 550 mq of white powder, mp 193°-194° C. (dec.).

EXAMPLE 31

N-[2-[1,1'-Biphenyl]-4-yl)ethyl]-N'-hydroxy-N'-methylurea

A mixture of 4-phenylbenzaldehyde (5.17 g, 28.4 mmol), malonic acid (4.0 g), pyridine (20 ml), and piperidine (0.5 ml) was heated until gas evolution began. Heating was continued until gas evolution ceased (about 30 minutes at 90°-100° C.). The mixture was cooled, and the solid product triturated with boiling methanol (150 ml) and enough concentrated HCl to make the mixture acidic. The mixture was cooled, and the product collected by filtration, washed with water and methanol, and dried in vacuo to provide 4-phenylcinnamic acid (4.85 g, 76% yield), mp 220°-225° C. This material was dissolved in ethanol (150 ml) containing concentrated sulfuric acid (0.5 ml) and triethyl orthoacetate (3.5 ml), and refluxed for 24 hours. Removal of the solvent and recrystallization of the residue from methanol-water provided the ethyl ester (5.0 g, 92% yield), mp 88°-89° C.

A mixture of this ester (2.0 g, 7.9 mmol) and magnesium turnings (3.0 g, 123 mmol) in methanol (100 ml) was stirred at room temperature under nitrogen for three days, during which time the metal dissolved completely. The mixture was brought to reflux, and potassium hydroxide (9.0 g) was added in portions. After two hours, the mixture was diluted with water (100 ml), made acidic with concentrated HCl and refluxed until homogeneous. The mixture was diluted with another 50 ml of water, filtered hot and partially evaporated. Cooling and collecting the precipitate by filtration provided 3-([1,1'-biphenyl]-4-yl)propionic acid (0.72 g, 36% yield), mp 143°-149° C.

By the method of Example 30 above, this acid was converted into the title compound, and recrystallized from methanol-water to provide shiny flakes (0.56 g, 65% yield), mp 157°-158° C.

EXAMPLE 32

O

N-[3-([1,1'-Biphenyl]-4-yl)propyl]-N'-hydroxy-N'-methylurea 3-([1,1'-biphenyl]-4-yl)propionic acid from Example 31 above was converted to the amide via the acid chloride, and reduced with LiAlH4 in refluxing THF to provide 3-([1,1'-biphenyl]-4-propylamine, isolated as the hydrochloride salt by crystallization from methanol water. This hydrochloride salt (0.45 g, 1.8 mmol) was added to 20% phosgene in toluene (10 ml) and stirred for 16 hours at 75° C. under nitrogen. The resulting solution was evaporated, leaving the isocyanate as a yellow oil. This was dissolved in methylene chloride (15 ml) and treated with N-methylhydroxylamine as in Example 30 above to provide, after crystallization from water-methanol and then from 1,2-dichloroethane, the title compound as a white powder (0.24 g, 47% yield), mp 170°-172° C. (dec).

EXAMPLE 33

N-[2-([1,1'-biphenyl]-4-yloxy)ethyl]N'-hydroxy-N'-methylurea

To a solution of 4-phenylphenol (3.4 g, 20 mmol) in DMF (75 ml) was added sodium hydride (0.88 g of a 60% dispersion in oil, 22 mmol). The mixture was stirred at 70° C. under nitrogen until a clear solution was obtained, then cooled to 50° C. To the mixture was added chloroacetonitrile (1.5 ml, 24 mmol). A precipitate formed immediately. The mixture was cooled to room temperature, poured into water (300 ml), and extracted with ether. The ether extracts were dried (MgsO4), filtered and evaporated. Recrystallization of the residue from methanol provided [1,1'-biphenyl]-4yloxyacetonitrile, mp 81°-83° C.

This nitrile was dissolved in THF (50 ml), and 15 ml of 1M borane in THF was added. The mixture was refluxed under nitrogen for four hours, cooled, made acidic by slow addition of concentrated HCl, and refluxed another 30 minutes. The solvent was evaporated, and the residue recrystallized from ethanol to provide 2-([1,1'-biphenyl]4-yloxy)ethylamine hydrochloride as white flakes (1.7 g 34% yield from the phenol), mp >300° C.

This hydrochloride was converted to the title compound by treatment with phosgene and N-methylhydroxylamine as in Example 32 above. Recrystallization from methanol-water provided a white powder (0.46 g, 25% yield), mp 178°-179° C. (dec).

EXAMPLE 34

N-[3-([1,1'biphenyl]-4-yloxy)propyl]N'hydroxy N'methylurea

A mixture of 4-phenylphenol (0.8 g, 57.6 mmol), potassium carbonate (30 g, 220 mmol), and ethyl 4-bromobutyrate (20 ml, 140 mmol) in DMF (100 ml) was stirred for 16 hours at 95° C. under nitrogen. The mixture was cooled, poured into water (400 ml) and extracted with 1:2 ether-hexane (250 ml). The extracts were dried (MgsO4), and filtered through a pad of silica gel to remove the colored impurities. The filtrate was concentrated to an oil, which was dissolved in methanol, concentrated again, and redissolved in 500 ml methanol. To this was added water (100 ml) and potassium hydroxide (10 g), and the mixture refluxed for five hours. On cooling, the potassium salt of 4-([1,1'-biphenyl]-4-yloxy)butanoic acid separated out and was collected by filtration, washed with water, and dried in vacuo to provide 8.9 g (52%) of white powder, mp >300° C. Acidification of the filtrates provided the free acid (2.5 g), mp 155.5°-157.5° C.

The potassium salt (2.5 g, 8.5 mmol) was treated with oxalyl chloride, sodium azide and N-methylhydroxylamine as in Example 30 above to provide, after crystallization from methanol, the title compound as a white powder (1.72 g, 67% yield), mp 161°-162° C.

EXAMPLE 35

N-[4-([1,1'-Biphenyl]-4-yloxy)butyl]N'-hydroxy-N'-methylurea

A mixture of N-(4-bromobutyl)phthalimide (14.1 g, 50 mmol), 4-phenylphenol (8.5 g, 50 mmol), and potassium carbonate (15.0 g, 108 mmol) in DMF (75 ml) was stirred under nitrogen for 16 hours at 85° C., then water (200 ml) was added dropwise to the cooled solution.

The precipitate was collected by filtration, and recrystallized from methanol-water to provide N-[4-(1,1'-biphenyl]-4-yloxy)butyl]phthalimide as an off-white solid (11.94 g, 64% yield), mp 114°-115° C.

A solution of this material (11.8 g, 31.8 mmol) and hydrazine (1.3 g, 40 mmol) in ethanol (400 ml) was stirred for two days at 74° C., cooled to room temperature, and the precipitate collected by filtration. This mixture was suspended in a mixture of ethanol (100 ml) and 1N HCl (50 ml), heated to boiling, and filtered while hot to remove phthalhydrazide. The filtrate was made alkaline with NaOH, diluted with water (100 ml), and extracted with methylene chloride. The methylene chloride solution was dried (MgSO$_4$), filtered and evaporated, and the residue dissolved in 50 ml boiling 1N HCl. On cooling, a solid precipitated out, and was collected and dried in vacuo to provide 4-([1,1'-biphenyl]-4-yloxy)butylamine hydrochloride as shiny flakes (5.33 g, 91% yield), mp 262°-264° C.

This hydrochloride (1.00 g, 3.6 mmol) was converted to the title compound by the method of Example 32 above, giving after crystallization from methanol-dibutyl ether a white powder (175 mg, 15% yield), mp 168°-169° C.

EXAMPLE 36

N-[5-([1,1'Biphenyl]-4-yloxy)pentyl]N'-hydroxy-N'-methylurea

By the method of Example 34, sodium 6-([1,1'-biphenyl]-4-yloxy)hexanoate was prepared from ethyl 6-bromohexanoate and 4-phenylphenol, and then converted to the title compound, obtained as white flakes from 1,2-dichloroethane, mp 153°-154° C.

EXAMPLE 37

N-[6-([1,1'-Biphenyl]-4-yloxy)hexyl]N'hydroxy-N'-methylurea

By the method of Example 34, 7-([1,1'-biphenyl]-4-yloxy)-heptanenitrile was prepared from 7-bromoheptanenitrile and 4-phenylphenol, as shiny flakes from water-methanol, mp 78°-79° C. This material (3.0 g, 10.7 mmol) was heated in ethylene glycol (100 g) containing water (33 ml) and NaOH (10 g). After four hours at reflux, during which the nitrile dissolved and a solid formed, the mixture was cooled, diluted with water (400 ml), and acidified with acetic acid (100 ml). The precipitate was collected by filtration, and dried in vacuo to provide 7-([1,1'-biphenyl]-4-yloxy)heptanoic acid as a white solid (3.1 g 97% yield).

This acid was converted by the method of Example 30 above to the title compound. Recrystallization from methanol and then from 1,2-dichloroethane provided a white powder, mp 148°-150° C.

EXAMPLE 38

N-([1,1'-Biphenyl]-4-yloxy)heptyl]-N'-hydroxy-N'-methylurea 7-([1,1'-Biphenyl]-4-yloxy)heptanenitrile, prepared as in Example 37 above, was reduced with borane in THF to the amine, and isolated as the hydrochloride salt, mp 228°-230° C. This was converted to the title compound by the method of Example 32 above, and recrystallization from methylene chloride provided white crystals, mp 152°-153° C.

EXAMPLE 39

N-[7-(Benzyloxy)heptyl]-N'hydroxy-N'-methylurea

By the method in Example 29 above, 6-(benzyloxy)-1-hexanol was converted to the corresponding methanesulfonate, and this was then converted to 7-(benzyloxy)heptanenitrile by treatment with sodium cyanide in dimethylsulfoxide at 100° C. for one hour. The nitrile was then converted to 7-(benzyloxy)heptylamine hydrochloride by the method in Example 38 above.

By the method of Example 32 above, 7-(benzyloxy)heptylamine hydrochloride was converted to the isocyanate by treatment with phosgene in toluene, and then treated with N-methylhydroxylamine. Chromatography on silica gel, and recrystallization from ethyl acetate-hexane, provided the title compound as a white solid, mp 69°-70.5° C.

EXAMPLE 40

N-[2-(3,4-Dimethoxyphenyl)ethyl]N'-hydroxy-N'-methylurea

To a stirred solution of 3-(3,4-dimethoxyphenyl)propionic acid (90.0 g, .428 mol) in acetone (400 ml) under nitrogen at −20° C. was added triethylamine (62.0 ml, 1.04 equiv.), and then dropwise ethyl chloroformate (42.3 ml, 1.01 equiv.), maintaining the temperature below −20° C. The resulting slurry was stirred for an additional 20 minutes and then a chilled solution of sodium azide (42.8 g, 1.5 equiv.) in water (125 ml) was added, keeping the temperature below −10° C. After an additional 20 minutes, the mixture was poured into 1500 ml of ice water, and extracted three times with benzene (500 ml). The combined extracts were dried (Na$_2$SO$_4$) and filtered through MgSO$_4$.

The filtrate was heated to reflux under a Dean-Stark trap, removing the first 500 ml of distillate. The solution was refluxed for an additional hour, cooled and evaporated. The residue was dissolved in methylene chloride (50 ml) and added slowly to a solution of N-methylhydroxylamine hydrochloride (35.9 g, 1.0 equiv.) and triethylamine (62.0 ml, 1.04 equiv.) in methylene chloride (750 ml). After 16 hours, the reaction mixture was washed three times with 10% aqueous citric acid (250 ml), dried (MgSO$_4$), filtered and evaporated. Recrystallization from ethyl acetate-hexane provided the title compound as a white solid (72.85 g, 67% yield), mp 103°-104° C.

EXAMPLE 41

N-[2-(3,4-Dimethoxyphenyl)ethyl]-N'-hydroxy-N'-(1-methylethyl)urea

To a stirred solution of 3-[3,4-dimethoxyphenyl) propionic acid (5.26 g, 25.0 mmol) in acetone (40 ml) was added triethylamine (3.6 ml, 1.04 equiv.). The mixture was cooled to −20° C., and ethyl chloroformate (2.4 g, 1.02 equiv.) was added dropwise so as to keep the temperature below −15° C. The resulting slurry was stirred for 15 minutes, and a chilled solution of sodium azide (2.5 g, 1.5 equiv.) in water (10 ml) was added. After 15 minutes, the mixture was poured into ice water (200 ml), extracted twice with toluene (50 ml), and the combined extracts dried (Na$_2$SO$_4$), filtered through MgSO$_4$, and the filtrate heated to reflux under a Dean-Stark trap, discarding the first 10 ml of distillate. After 30 minutes at reflux, the solution was cooled and a solution of benzyloxyamine (3.1 g) in chloroform (25 ml) was added.

After 10 minutes, the solution was evaporated in vacuo. Trituration of the residue with hexane provided N-3,4-dimethoxyphenyl)ethyl)-N'benzyloxyurea as a white solid (7.14 g, 86% yield), mp 79°–81° C.

To a stirred solution of this product (1.65 g, 5.0 mmol) in DMF (15 ml) under nitrogen at room temperature was added sodium hydride (220 mg of a 60% dispersion in oil, 1.1 equiv.). After 15 minutes, 2-iodopropane (0.6 ml) was added, and the reaction mixture was heated to 70° C. and stirred for 16 hours. The mixture was cooled and poured into water (200 ml), and extracted twice with ether. The combined extracts were dried (MgsO4), filtered and evaporated.

Purification by chromatography on silica gave N-isopropyl-N-benzyloxy-N'-[2-(3,4-dimethoxyphenyl)ethyl]urea as a colorless oil (1.13 g, 61% yield). Hydrogenolysis as in Example 2 above provided the title compound after recrystallization from ethyl acetate-hexane as a white solid, mp 113°–114° C.

EXAMPLE 42

N-[(3,4-Dimethoxyphenyl)methyl]-N'-hydroxy-N'-methylurea

Using the method of Example 18 above, but using 3,4-dimethoxyphenylacetyl chloride, the title compound was obtained after recrystallization from ethyl acetate as a light yellow solid, mp 132°–133° C.

EXAMPLE 43

N-[2-(3,4-Methylenedioxy)phenyl)ethyl-N'-hydroxy-N'-methylurea

Using the method of Example 41 above, but using 3-(3,4- C methylenedioxyphenyl)propionic acid and methyl iodide, the named compound was obtained after recrystallization from hexane, mp 99°–100° C.

EXAMPLE 44

N-[2-(2,3-Dimethoxyphenyl)ethyl]-N'-hydroxy-N'-methylurea

Using the method of Example 41 above, but using 3-(2,3-di-methoxyphenyl)propionic acid and methyl iodide, the title compound was obtained after recrystallization from ethyl acetate-hexane, mp 83°–85° C.

EXAMPLE 45

N-[2-(3,4,5-Trimethoxyphenyl)ethyl]-N'-hydroxy-N'-methylurea

Using the method of Example 41 above, but using 3-(3,4,5-trimethoxyphenyl)propionic acid and methyl iodide, the named compound was obtained after crystallization from hexane, mp 100°–102° C.

EXAMPLE 46

N-[2-(Benzo-1,4-dioxan-6-yl)ethyl]-N'-hydroxy-N'-methylurea

Using the method of Example 40, but using 3-(benzo-1,4-dioxan-6-yl)propionic acid, the title compound was obtained after purification by chromatography on silica as a white solid, mp 94°–95° C.

EXAMPLE 47

N-[2-(2,5-Dimethoxyphenyl)ethyl]-N'-hydroxy-N'-methylurea

Using the method of Example 40, but using 3-(2,5-dimethoxyphenyl)propionic acid, the named compound was obtained after purification by chromatography on silica as a white solid, mp 73°–74° C.

EXAMPLE 48

N-[2-(3,5-Dimethoxyphenyl)ethyl]-N'-hydroxy-N'-methylurea

Using the method of Example 40, but using 3-(3,5-dimethoxyphenyl)propionic acid, the title compound was obtained after recrystallization from ethyl acetate-hexane as a white solid, mp 121°–123° C.

EXAMPLE 49

N-[2-(2,4-Dimethoxyphenyl)ethyl]-N'-hydroxy-N'-methylurea

Using the method of Example 40, but using 3-(2,4-dimethoxyphenyl)propionic acid, the named compound was obtained after purification by recrystallization from ethyl acetate-hexane as a white solid, mp 83°–84° C.

EXAMPLE 50

N-[2-(3,4-Dichlorophenyl)ethyl]-N'-hydroxy-N'-methylurea

To a solution of lithium diisopropylamide (54 mmol) in THF (100 ml) at 0° C. was added acetic acid (1.62 g, 27 mmol). The solution was stirred for 30 minutes, then heated to 35° C. for 15 minutes, then cooled to −60° C. 3,4-Dichlorobenzyl chloride (5.4 g, 27.5 mmol) was added, and the mixture was allowed to warm to room temperature. After 18 hours, 1N HCl (55 ml) was added, and the mixture was evaporated. The oily residue was dissolved in ether and acidified with 1N HCl to pH 1, extracted twice with ether, and the combined extracts washed with 1N NaOH (60 ml). The aqueous solution was washed once with ether, then acidified with 1N HCl (75 ml). A solid formed which was extracted into methylene chloride and the extract was dried (MgSO4), filtered and evaporated to give a 5:2 mixture of 3-(3,4-dichlorophenyl)propionic acid and bis(3,4-dichlorobenzyl)acetic acid as a light yellow solid.

Using the method of Example 40, this mixture of acids was converted to the title compound, obtained after purification by chromatography on silica as the more polar fraction, a white solid, mp 108°–109° C.

EXAMPLE 51

6,7-Dimethoxy-N-hydroxy-N-methyl-1,2,3,4-tetrahydroisoquinoline-2-carboxamide

To 20% phosgene in toluene (30 ml) was added 6,7-dimethoxy-1,2,3,4 tetrahydroisoquinoline hydrochloride (4.6 q, 20 mmol). The mixture was heated to 75°–80° C. under nitrogen for two hours, whereupon an additional 10 ml of the 20% phosgene solution was added. After an additional two hours, a clear solution formed, which was cooled and stirred overnight. The solution was evaporated, and the residue redissolved in ether, filtered through Celite, and the filtrate evaporated to give the carbamyl chloride as a yellow oil (5.08 q, 99% yield).

To a stirred slurry of N-methylhydroxylamine hydrochloride (3.34 g, 40.0 mmol) in methylene chloride (30 ml) was added triethylamine (5.6 ml, 40.0 mmol) and to this was added a solution of the carbamyl chloride in methylene chloride (30 ml). After 30 minutes, ethyl acetate (120 ml) was added, and the slurry filtered. The filtrate was washed twice with 10% aqueous citric acid, dried (MgsO4), filtered and evaporated. Trituration of the residue with ether gave the title compound as a tan solid (3.98 g, 75% yield), mp 101°-102° C.

EXAMPLE 52

N-[2-(3,4-Dimethoxyphenyl)ethyl]-N'-acetoxy-N'-t-butylurea

Using the method of Example 40, but using N-acetoxy-tbutylamine, the title compound was obtained after purification by chromatography on silica as a white solid, mp 123°-125° C.

EXAMPLE 53

N-[2-(3,4-Dimethyoxyphenyl)ethyl]-N'-hydroxy-N,N'-dimethylurea

Using the method of Example 51, but using 2-(3,4-dimethoxyphenyl)ethylamine, the named compound was obtained after recrystallization from ethyl acetate-hexanes as a white solid, mp 73°-74° C.

EXAMPLE 54

N-[2-(3,4-Dimethoxyphenyl)-1-methylethyl]-N'-hydroxy-N'-methylurea

Using the method of Example 40, but using 3-(3,4-dimethoxyphenyl)-2-methylpropionic acid, the title compound was obtained after purification by chromatography on silica as a white solid, mp 78°-80° C.

EXAMPLE 55

N-[2-[3-Methoxy-4-(2-propenoxy)phenyl]ethyl]-N'-methylurea

Using the method of Example 40, but using 3-[3-methoxy-4-(2-Propenoxy)phenyl]propionic acid, the named compound was obtained after purification by chromatography on silica and recrystallization from methylene chloride-hexane as a white solid, mp 81°-83° C.

EXAMPLE 56

N-[2-(3,4-Dimethoxyphenyl)-1,1-dimethylethyl]-N'hydroxy-N'-methylurea

Using the method of Example 40, but using 3-(3,4-dimethoxyphenyl)-2,2-dimethylpropionic acid, the title compound was obtained after purification by chromatography on silica and recrystallization from ethyl acetate-hexane as a white solid, mp 77°-78° C.

EXAMPLE 57

N-(5,6-Dimethoxyindan-2-yl)-N'-hydroxy-N'-methylurea

To a solution of dimethyl malonate (1.7 ml, 14.9 mmol) in DMF (30 ml) at room temperature under nitrogen was added sodium hydride (1.3 g of a 60% dispersion in oil). The mixture was stirred for 20 minutes, and 1,2-bis(chloromethyl)-4,5-dimethoxybenzene (3.5 g, 14.9 mmol) was added. After 16 hours, the mixture was quenched with water and extracted three times with ether. The combined extracts were washed twice with water and dried (McSO4), filtered and evaporated. The residue was dissolved in methylene chloride and filtered through a pad of silica gel. Evaporation gave dimethyl 5,6-dimethoxyindane-2,2-dicarboxylate as a white solid (2.24 g, 55% yield).

To this diester (2.40 g) in DMSO (16 ml) was added sodium chloride (835 mg) and water (0.41 ml). The mixture was heated to 170°-180° C. for three hours, cooled and poured into ice water (100 ml). The mixture was extracted four times with ether, and the combined extracts were washed with water, dried (MgSO4), filtered and evaporated. The residue was dissolved in methanol (10 ml) and 1N NaOH (10 ml) was added. The mixture was refluxed for one hour, cooled and partially evaporated. Water was added to the residue, and the mixture was extracted once with ether. The aqueous phase was acidified with 1N HCl (15 ml) and extracted with methylene chloride. The extracts were dried (MgsO4), filtered and evaporated to give 5,6-dimethoxyindane-2-carboxylic acid as a tan solid (1.29 g, 86% yield), mp 133°-135° C.

By the method of Example 40, this acid was converted to the title compound, obtained after recrystallization from methylene chloride-hexane as a white solid, mp 165°-166° C.

EXAMPLE 58

N-[trans-3-(3,4-Dimethoxyphenyl)bicyclo[2.2.1]-5-hepten-2-yl]-N'-hydroxy-N'-methylurea By the method of Example 40, trans-3-(3,4-dimethoxyphenyl)bicyclo[2,2,1]-5-heptenyl-2-carboxylic acid (a 1:1 mixture of diastereomers) was converted to the named compound, isolated by chromatography on silica as a yellow glass. The product is a 1:1 mixture of diastereomers.

EXAMPLE 59

N-[trans-3-(3,4-Dimethoxyphenyl)bicyclo[2.2.1]-heptan-2-yl]-N'-hydroxy-N'-methylurea Using the hydrogenolysis procedure described in Example 2, the compound of Example 58 above was hydrogenated to give the title compound, isolated by chromatography on silica as a colorless glass. The product is a 1:1 mixture of diastereomers.

EXAMPLE 60

N-[(5,6-Dimethoxyindan-1-yl)methyl]-N'-hydroxy-N'-methylurea

To a solution of ethyl 5,6-dimethoxy-1indanylideneacetate (5.12 g, 19.5 mmol) in methanol (100 ml) under nitrogen at 10° C. was added magnesium turnings (0.96 g). The mixture was stirred for two hours and 1N NaOH (25 ml) was added. After 16 hours, the slurry was acidified with 1N HCl (100 ml) and evaporated. Water was added, and the mixture was extracted three times with methylene chloride. The combined extracts were dried (MgsO4), filtered and evaporated, to give 5,6-dimethoxy-1-indanylacetic acid as a colorless oil (3.21 g, 70% yield). By the method of Example 40, this acid was converted to the title compound, recrystallized from 1,2-dichloroethane-hexane as a white solid, mp 120°-121° C.

EXAMPLE 61

N-(6,7-Dimethoxy-1,2,3,4-tetrahydro-2-naphthyl)-N'-hydroxy-N'-methylurea

To 20% phosgene in toluene (10 ml) was added 6,7-dimethoxy-1,2,3,4-tetrahydro-2-naphthylamine hydrochloride (404 mg). The mixture was refluxed until homogenous, then evaporated. The residue was dissolved in methylene chloride (5 ml) and added to a stirred solution of N-methylhydroxylamine hydrochloride (200 mg) and triethylamine (0.33 ml) in methylene chloride (5 ml). After 30 minutes, the mixture was diluted with methylene chloride, and washed with 10% aqueous citric acid. The organic solution was dried (MgSO₄), filtered and evaporated. Purification by chromatography on silica and recrystallization from ethyl acetate-hexane gave the title compound as a white solid (255 mg), mp 150°–151° C.

EXAMPLE 62

7,8-Dimethoxy-N-hydroxy-N-methyl-1,2,4,5-tetrahydro-3H-3-benzazepine-3-carboxamide By the method of Example 51, 7,8-dimethoxy-1,2,4,5-tetrahydro-3H-3-benzazepine hydrochloride was converted to the title compound. Purification by chromatography on silica provided a white solid, mp 95°–96° C.

EXAMPLE 63

N,N-Bis-[3-(3,4-dimethoxyphenyl)propyl]-N'-hydroxy-N'-methylurea

By the method of Example 51, bis[3-(3,4-dimethoxyphenyl)propyl]amine hydrochloride was converted to the title compound. Recrystallization from ethyl acetate-hexane provided a tan solid, mp 93°–94° C.

EXAMPLE 64

N-[2-(3,4-Dimethoxyphenyl)ethyl]-N'-hydroxy-N'-methyl-N-(2-methylpropyl)urea

By the method of Example 51, N-[2-(3,4-dimethoxyphenyl)ethyl]isobutylamine hydrochloride was converted to the named compound and isolated by chromatography on silica as a light yellow oil.

EXAMPLE 65

N-[3-(3,4-Dimethoxyphenyl)propyl]-N'-hydroxy-N'-methylurea

By the method of Example 40, 4-(3,4-dimethoxyphenyl)butanoic acid was converted to the title compound. Recrystallization from ethyl acetate-hexanes provided a white solid, mp 99°–100° C.

EXAMPLE 66

N-[Trans-2-(3,4-dimethoxyphenyl)cyclopropyl]-N'-hydroxy-N'-methylurea

By the method of Example 40, trans-2-(3,4-dimethoxyphenyl)cyclopropanecarboxylic acid was converted to the named compound. Recrystallization from 1,2-dichloroethanehexanes gave a tan solid, mp 142°–144° C.

EXAMPLE 67

N-[2-(3,4-Dimethyloxyphenyl)ethyl]-N-(4-chlorophenyl)-N'-methyl-N'-hydroxyurea

By the method of Example 51, N-[2-(3,4-dimethoxyphenyl)ethyl]-4-chloroaniline hydrochloride was converted to the title compound. Purification by chromatography on silica provided a light yellow glass.

EXAMPLE 68

N-[2-(4-Benzyloxy-3-methoxyphenyl)ethyl]-N'-hydroxy-N'-methylurea

By the method of Example 40, 3-(4-benzyloxy-3-methoxyphenyl)propionic acid was converted to the named compound. Purification by chromatography on silica gave a white solid, mp 109°–111° C.

EXAMPLE 69

N-[2-(3-Benzyloxy-4-methoxyphenyl)ethyl]-N'-hydroxy-N'-methylurea

By the method of Example 40, 3-(3-benzyloxy-4-methoxyropionic acid was converted to the title compound. Crystallization from 1,2-dichloroethane-hexane provided a white solid, mp 125°–126° C.

EXAMPLE 70

N-[2-(4-Hydroxy-3-methoxyphenyl)ethyl]-N'-hydroxy-N'-methylurea

Hydrogenolysis of the compound of Example 68 above by the method of Example 2 above, and purification by chromatography on silica, gave the named compound as a white solid, mp 106°–107° C.

EXAMPLE 71

N-[2-(3-Hydroxy-4-methoxyphenyl)ethyl]-N'-hydroxy-N'-methylurea

Hydrogenolysis of the compound of Example 69 above by the method of Example 2 above, and purification by chromatography on silica, provided the title compound as a white solid, mp 178°–180° C.

EXAMPLE 72

N-[2-(3,4-Dimethoxyphenyl)ethyl]-N'-hydroxyurea

By the method of Example 40, but using N,O-bis(trimethylsilyl)hydroxylamine, and refluxing the product in 1N HCl for one hour, the title compound was obtained after recrystallization from ethyl acetate as a light yellow solid, mp 109°–111° C.

EXAMPLE 73

N-Hydroxy-3-(3-methoxyphenyl)-N-methylpiperidine-1-carboxamide

By the method of Example 51, 3-(3-methoxyphenyl)piperidine hydrochloride was converted to the title compound. Recrystallization from methylene chloride-hexanes provided a white solid, mp 96°–98° C.

EXAMPLE 74

N-[2-(3,4-Dimethoxyphenyl)ethyl]-N'-[3-(ethoxycarbonyl)propyl]-N'-hydroxyurea

Ethyl N-benzyloxy-4-aminobutyrate hydrochloride from Example 19 above (661 mg, 2.24 mmol) was added to 20% phosgene in toluene (5 ml), and the mixture was heated to 70° C. under nitrogen. After one hour, the solution was cooled and evaporated, and the residue was dissolved in methylene chloride (3 ml). This solution was added to a stirred solution of 2-(3,4-dimethoxyphenyl)ethylamine (440 mg, 1.0 equiv.) and triethylamine (0.4 ml, 1.2 equiv.) in methylene chloride (5 ml) at room temperature. After one hour, the reaction was diluted with methylene chloride and washed once with 10% aqueous citric acid. The organic solution was dried (MgSO₄), filtered and evaporated to give a colorless oil (1.02 g, 95% yield). Hydrogenolysis of this material by the procedure in Example 2 above, and recrystallization from chloroform-hexane, provided the title compound as a white solid (675 mg, 85% yield), mp 75°–76° C.

EXAMPLE 75

4-(Diphenylmethyl)-N-hydroxy-N-methylpiperidine-1-carboxamide

By the method of Example 51, 4-(diphenylmethyl)-piperidine was converted to the named compound, and recrystallized from hexane-ethyl acetate to provide a white solid, mp 143°-144° C.

EXAMPLE 76

N-Hydroxy-N-methyl-N'-[2-(3-phenoxyphenyl)ethyl]urea

By the method of Example 40, 3-(3-phenoxyphenyl)-propionic acid was converted to the title compound. Recrystallization from 1,2-dichloroethane/hexane provided a white solid, mp 84.5°-86° C.

EXAMPLE 77

Inhibition of 5-lipoxygenase

The inhibition of 5-lipoxygenase was tested in a cell-free homogenate by the procedure of B. Jakschik et al., Biochem.Biophys.Res.Comm. 95, 103 (1980). Basically, rat basophilic leukemia cells (RBL-1 cells) were maintained in culture in a suitable medium, and were collected by centrifugation prior to assay. The cell-free homogenate was prepared by sonication of the cells followed by centrifugation at 40,000 xg. The $CaCl_2$ dependent production of lipoxygenase products from $^{14}C$-arachidonic acid in the 40,000 xg supernatant was monitored in the presence of buffer (or other vehicle) or drug. Products were isolated by acidification and extraction, followed by thin layer chromatography. Radioactive areas corresponding to the authentic lipoxygenase products were quantitated by liquid scintillation counting. Data was reported as the $IC_{50}$, the concentration causing 50% inhibition of the generation of lipoxygenase products. The results are shown it Table I as the percent inhibition at 3 $\mu M$ or the amount of compound necessary to cause 50% inhibition.

EXAMPLE 78

Pulmonary Mechanics Assay

The bronchodilating activity of the compounds was tested in a pulmonary mechanics assay. Basically, male Hartley guinea pigs (about 400-500 g) were anesthetized with urethane (2 g/kg, i.p.) and placed in a whole body Plethysmograph. Cannulations of a jugular vein and carotid artery were performed for compound administration and monitoring blood pressure, respectively. The trachea was cannulated for respiration at a constate volume via a miniature starling pump. A Validyne differential pressure transducer ($\pm 20$ cm $H_2O$) sensed transpleural pressure via a 15 gauge needle inserted into the pleural cavity and a sidearm from the tracheal cannula. Tidal volume was sensed by another Validyne differential pressure transducer ($\pm 2$ cm $H_2O$) from pressure changes inside the plethysmograph. An on-line Buxco pulmonary mechanics computer calculated air flow, dynamic lung compliance and lung resistance. The values were recorded on a print-out.

The guinea pigs were pretreated with succinyl choline (1.2 mg/kg, i.v.) to arrest spontaneous respiration. A control challenge of arachidonic acid (0.5-1.0 mg/kg, i.v.) was administered, and the animals were then dosed with the test compound by various routes. At least 10 minutes were allowed to expire between arachidonic acid challenges. A second challenge was given and compared to the control response. This comparison was indicative of cyclooxygenase inhibition. Indomethacin (10 mg/kg, i.v.) was administered immediately after the second challenge. A third challenge of a higher dose of arachidonic acid (5-10 mg/kg, i.v.) was given. This response was induced by SRS-A and compared to the responses elicited by a separate control group of animals. Activity was indicative of lipoxygenase inhibition. Propranolol (0.005 mg/kg. i.v.) may be given prior to the third challenge to enhance the response to SRS-A.

Bronchoconstriction induced by arachidonic acid with or without indomethacin was expressed as maximum percent change in dynamic lung compliance (Cdyn) and maximum percent increase in lung resistance ($R_L$). Each guinea pig served as its own control for cyclooxygenase evaluation. The results are shown in Table I and are expressed as the percent inhibition of control.

EXAMPLE 79

Arachidonic Acid-Induced Ear Edema Assay

The topical anti-inflammatory activity of a compound was determined by its ability to inhibit an experimentally-induced inflammation in the mouse ear. Basically, four milligrams of arachidonic acid in acetone were applied to the dorsal surface of one ear with a microliter pipette. The mice were sacrificed at various times after application of arachidonic acid (one-half to six hours). A section of each ear was removed with a 7 mm round punch and weighed on an electronic or analytical balance. The difference in weight between treated and untreated ears was determined. Compounds to be evaluated for anti-inflammatory activity can be incorporated directly into the irritant mixture or at various times prior to or after application of arachidonic acid.

The degree of anti-inflammatory activity is shown in Table I, and is expressed in terms of the percent inhibition of ear weight increase.

TABLE I

| | Inhibition of 5-Lipoxygenase | | Inhibition of Arachidonate-Induced Ear Edema | | Inhibition of Arachidonate-Induced Bronchospasm | | | |
|---|---|---|---|---|---|---|---|---|
| | | | | | (IV Dosing) | | (ID Dosing) | |
| Ex. No. | % Inh. @ 3 $\mu M$ | $IC_{50}$ ($\mu M$) | % Inh. ($\mu g$ topically) | $ED_{50}$ ($\mu g$) | % Inh. w/wo Indomethacin | Dose, mg/kg | % Inh. w/wo Indomethacin | Dose, mg/kg |
| 1 | 100 | | 52 (400) | | 38/54 | 15 | | |
| 2 | | 0.09 | 82 (400) | 29 | 44/32 | 15 | | |
| 3 | 100 | | 51 (400) | | | | | |
| 4 | 100 | | 65 (400) | | <20/−39 | 15 | | |
| 5 | 100 | | 49 (400) | | 37/<20 | 15 | | |
| 6 | 100 | | 30 (400) | | <20/−45 | 15 | | |
| 7 | 77 | 1.8 | | 49 | 41/61 | 15 | | |
| 8 | 93 | | 95 (200) | | | | | |

TABLE I-continued

BIOLOGICAL ACTIVITY OF HYDROXYUREAS

| | Inhibition of 5-Lipoxygenase | | Inhibition of Arachidonate-Induced Ear Edema | | Inhibition of Arachidonate-Induced Bronchospasm | | | |
|---|---|---|---|---|---|---|---|---|
| | | | | | (IV Dosing) | | (ID Dosing) | |
| Ex. No. | % Inh. @ 3 μM | IC$_{50}$ (μM) | % Inh. (μg topically) | ED$_{50}$ (μg) | % Inh. w/wo Indomethacin | Dose, mg/kg | % Inh. w/wo Indomethacin | Dose, mg/kg |
| 9 | 64 | | | 55 | | | | |
| 10 | 100 | | | | | | | |
| 11 | | 0.1 | 90 (400) | 43 | 98/95 | 15 | −46/36 | 50 |
| 12 | 100 | | 94 (200) | 65 | | | 40/−9 | 50 |
| 13 | 95 | | 90 (200) | | 66/57 | 15 | | |
| 14 | 95 | | 95 (200) | 156 | | | 49/−128 | 50 |
| 15 | 100 | | 26 (200) | | | | 46/−26 | 50 |
| 16 | | 0.21 | 73 (400) | 28 | 58/55 | 15 | 35/<20 | 100 |
| 17 | | 0.16 | 88 (400) | 24 | 79/41 | 15 | | |
| 18 | 94 | | | | | | | |
| 19 | 94 | | 60 (400) | 183 | | | 0/−89 | 50 |
| 20 | 65 | | 47 (100) | | | | | |
| 21 | 22 | | | | | | | |
| 22 | 71 | | | | | | | |
| 23 | | (>10) | 29 (200) | | 52/97 | 15 | | |
| 24 | | 5.2 | 27 (200) | | | | | |
| 25 | | 0.74 | 81 (400) | 90 | 62/85 | 20 | | |
| 26 | | 0.7 | 30 (400) | | | | | |
| 27 | | 1.4 | 13 (400) | | | | | |
| 28 | 96 | 0.28 | 85 (400) | 134 | | | | |
| 29 | 30 | | | | | | | |
| 30 | 74 | | | | | | <20/<20 | 50 |
| 31 | 39 | | 40 (200) | | | | | |
| 32 | 71 | | | | | | <20/<20 | 50 |
| 33 | 70 | | | | | | 28/<20 | 50 |
| 34 | 93 | | | | | | 34/−74 | 50 |
| 35 | 79 | | | | | | 33/<20 | 50 |
| 36 | 67 | | | | | | 31/<20 | 50 |
| 37 | 65 | | | | | | −11/−33 | 50 |
| 38 | 56 | | | | | | <20/−9 | 50 |
| 39 | 100 | | 70 (200) | 31 | | | | |
| 40 | | 4.3 | 66 (400) | | 89/86 | 15 | 89/69 | 25 |
| 41 | 95 | | | | 70/42 | 15 | 30/<20 | 50 |
| 42 | 28 | | | | | | | |
| 43 | 65 | | | | | | <20/<20 | 50 |
| 44 | 33 | | | | | | 58/<20 | 50 |
| 45 | 36 | | | | | | | |
| 46 | 42 | | | | | | | |
| 47 | 56 | | | | | | | |
| 48 | 42 | | | | | | | |
| 49 | 99 | | | | 67/39 | 15 | | |
| 50 | 59 | | | | | | <20/<20 | 50 |
| 51 | 24 | | 28 (100) | | 60/<20 | 15 | | |
| 52 | 9 | | 69 (100) | | | | | |
| 53 | 0 | | | | 51/79 | 15 | 71/52 | 25 |
| 54 | 8 | | | | | | | |
| 55 | 42 | | | | 83/56 | 15 | 56/−68 | 50 |
| 56 | 3 | | 38 (100) | | | | | |
| 57 | 55 | | | | | | | |
| 58 | 37 | | | | | | 68/35 | 50 |
| 59 | 39 | | | | | | | |
| 60 | 51 | | | | 67/48 | 15 | | |
| 61 | 73 | | | | <20/<20 | 15 | | |
| 62 | 0 | | 35 (200) | | | | | |
| 63 | 76 | | | | | | 21/<20 | 50 |
| 64 | 33 | | | | | | | |
| 65 | 19 | | | | 89/86 | 15 | 59/52 | 50 |
| 66 | 28 | | | | 90/61 | 15 | 45/43 | 50 |
| 67 | 48 | | | | | | | |
| 68 | 69 | | | | | | 28/<20 | 50 |
| 69 | 41 | | 38 (200) | | | | | |
| 70 | 39 | | | | | | <20/<20 | 50 |
| 71 | 5 | | | | | | <20/77 | 50 |
| 72 | 21 | | | | | | 56/50 | 50 |
| 73 | 46 | | | | | | | |
| 74 | 42 | | | | | | | |
| 75 | 44 | | | | | | | |
| 76 | 66 | | | | | | | |

What is claimed is:

1. A hydroxyurea selected from the group consisting of

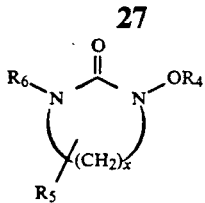

wherein
R$_4$ is hydrogen or lower alkanoyl,
R$_5$ is C$_5$ to C$_{10}$ alkyl or lower alkoxycarbonyl
R$_6$ is C$_1$ to C$_{10}$ alkyl.

2. A compound of claim 1 wherein R$_4$ is H.

3. A compound of claim 1 wherein R$_4$ is a C$_2$–C$_7$ alkanoyl group.

4. A compound of claim 3 selected from the group consisting of 1-pentyl-3-hydroxyimidazolidin-2-one, 1-octyl-3-hydroxyimidazolidin-2-one, 1-decyl-3-hydroxyimidazolidin-2-one, 1-decyl-3-hydroxy-3,4,5,6-tetrahydro-1H-pyrimidin-2-one, ethyl-3-decyl-1-hydroxyimidazolidin-2-one-4-carboxylate, 4-decyl-1-hydroxy-3-methylimidazolidin-2-one and 5-decyl-1-hydroxy-3-methyl-3,4,5,6-tetrahydro-1H-pyrimidin-2-one.

5. A method for dilating the broncho passages of a mammal which comprises administering to a mammal an effective amount of a compound of claim 1 selected from the group consisting of

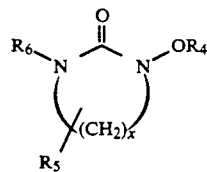

wherein R$_4$ is hydrogen or lower acyl, R$_5$ is C$_5$ to C$_{10}$ alkyl or lower alkoxycarbonyl, R$_6$ is C$_1$ to C$_{10}$ alkyl.

6. The method of claim 5 wherein R$_4$ is H.

7. The method of claim 5 wherein R$_4$ is an alkanoyl group.

8. The method of claim 5 wherein R$_2$ is H, R$_3$ is C$_1$–C$_{20}$ alkyl and R$_4$ is H.

9. The method of claim 5 wherein said compound is selected from the group consisting of 1-pentyl-3-hydroxyimidazolidin-2-one, 1-octyl-3-hydroxyimidazolidin-2-one, 1-decyl-3-hydroxyimidazolidin-2-one, 1-decyl-3-hydroxy-3,4,5,6-tetrahydro-1H-pyrimidin-2-one, ethyl-3-decyl-1-hydroxyimidazolidin-2-one-4-carboxylate, 4-decyl-1-hydroxy-3-methylimidazolidin-2-one and 5-decyl-1-hydroxy-3-methyl-3,4,5,6-tetrahydro-1H-pyrimidin-2-one.

10. A method for treating an inflammatory skin disease of a mammal which comprises topically administering to a mammal an effective amount of a compound of claim 1 or a pharmaceutically acceptable salt thereof.

* * * * *